(12) United States Patent
Kaiser et al.

(10) Patent No.: US 9,730,452 B2
(45) Date of Patent: Aug. 15, 2017

(54) METHODS TO INDUCE DROUGHT TOLERANCE IN CROPS

(71) Applicant: Valent BioSciences Corporation, Libertyville, IL (US)

(72) Inventors: Roger Kaiser, Round Lake, IL (US); Eric Ott, Greenfield, IN (US); Paul Silverman, Highland Park, IL (US); Jim Wargo, Atlanta, GA (US); Neil Badenhop, Pemberville, OH (US); Subbaiah Chalivendra, Baton Rouge, LA (US)

(73) Assignee: Valent BioSciences LLC, Libertyville, IL (US)

( * ) Notice: Subject to any disclaimer, the term of this patent is extended or adjusted under 35 U.S.C. 154(b) by 57 days.

(21) Appl. No.: 14/168,587

(22) Filed: Jan. 30, 2014

(65) Prior Publication Data

US 2014/0213454 A1    Jul. 31, 2014

Related U.S. Application Data

(60) Provisional application No. 61/759,063, filed on Jan. 31, 2013.

(51) Int. Cl.
*A01N 47/20*    (2006.01)
*A01N 43/90*    (2006.01)
*A01N 43/653*    (2006.01)
*A01N 45/00*    (2006.01)

(52) U.S. Cl.
CPC .................................. *A01N 45/00* (2013.01)

(58) Field of Classification Search
None
See application file for complete search history.

(56) References Cited

U.S. PATENT DOCUMENTS

| 2004/0219675 A1 | 11/2004 | Sainz et al. | |
|---|---|---|---|
| 2008/0318782 A1* | 12/2008 | Fugiel et al. | 504/136 |
| 2009/0104222 A1 | 4/2009 | Freund | |

FOREIGN PATENT DOCUMENTS

CN    102 674 944 A    9/2012

OTHER PUBLICATIONS

Kaya, Cengiz, A. Levent Tuna, and AC Alves Alfredo. "Gibberellic acid improves water deficit tolerance in maize plants." Acta physiologiae plantarum 28.4 (2006): 331-337.*
Maksymowych, R., and A. B. Maksymowych. "Induction of morphogenetic changes and acceleration of leaf initiation by gibberellic acid in Xanthium pennsylvanicum." American Journal of Botany (1973): 901-906.*
Wang et al., "Influence of water stress on endogenous hormone contents and cell damage of maize seedlings", Journal of Integrative Plant Biology, 2008, vol. 50, No. 4, pp. 427-434.
Khan et al. "Salinity stress resistance offered by endophytic fungal interaction between penicillium minioluteum LHL09 and glycine max", Journal of Microbiology and Biotechnology, 2011, vol. 21 No. 9pp. 893-902.
Hedded, "The genes of the green revolution", Trends in Genetics, vol. 19 No. 1, Jan. 2003, pp. 5-9.
Jiang et al., "Drought responses of perennial ryegrass treated with plant growth regulators", Hort Science, 33(2), 1998, pp. 270-273.
Kaya et al., "Gibberellic acid imporves water deficit tolerance in maize plants", APP ACTA Physiologiae Plantarium, vol. 28 No. 4, 2006, pp. 331-337.
Larson et al., "Ryzup on connon: report on trials, 1994-96", Abbott Laboratories, 1997 Beltwide Cotton Conferences, pp. 1474-1475.
Nagel et al., "Growth rate and biomass partitioning of wildtype and low-gibberellin tomato (*Solanum lycopersicum*) plants growing at a high and low nitrogen supply", Physiologiae Plantarium, 111: 2001, pp. 033-39.
Naghashzadeh et al., "Evaluation of effects of gibberellic acid on maize (*Zea mays* L.) in different planting dates", Plant Ecophysiology, 3, 2009, pp. 159-162.
Olszewski et al., "Gibberellin signaliing: biosynthesis, catabolism, and respone pathways", The Plant Cell, S61-S80, Supplement 2002.
Peng et al., "Green revolution genes encode mutant gibberellins response modulators", Macmillan Magazines Ltd., Nature vol. 400, Jul. 15, 1999, pp. 256-261.
Robertson et al., Effects of CCC on drought resistance of triticum aestivum, L and *Zea mays*,L., Ann. Bot. 37, 1973, pp. 929-934.
Sponsel, "Commercial uses of gibberellins", Plant Physiology Onliune, pp. 1-3.
Merritt, "Gibberellins for agriculture", Agriculture and Food Chemistry, vol. 6, No. 3, Mar. 1958, pp. 184-187.
Rademacher, "Growth retardants: effects of gibberellins biosynthesis and other metabolic pathways", Growth Retardants, pp. 501-531.
Ghodrat, et al., "Yield and Yield Components of Corn (*Zea mays* L.) in Response to Foliar Application with Indole Butyric Acid and Gibberellic Acid" American-Eurasian J. Agric. & Environ. Sci., 12 (9): 1246-1251, 2012.
Ghodrat et al., "Growth Analysis of Corn (*Zea mays* L.) as Influenced by Indole-Butyric Acid and Gibberellic Acid", J. Basic. Appl. Sci. Res., 3(2)180-185, 2013.
Soroushi et al., "The Interaction of Drought Stress and Gibberellic Acid on Corn (*Zea mays* L.)", World Academy of Science, Engineering and Technology (60) 142-143, 2011.

(Continued)

*Primary Examiner* — Sue Liu
*Assistant Examiner* — Daniel Branson
(74) *Attorney, Agent, or Firm* — Wood, Phillips, Katz, Clark & Mortimer

(57) ABSTRACT

The present invention is directed to methods for improving drought stress tolerance of a cereal grain comprising applying an effective amount of at least one gibberellin to the cereal grain during early vegetative growth stage. The present invention is also directed to methods for improving yield of a cereal grain comprising applying an effective amount of at least one gibberellin to the cereal grain during early vegetative growth stage.

6 Claims, No Drawings

(56) References Cited

OTHER PUBLICATIONS

EESR issued May 31, 2016 is corresponding EP Application No. 14746850.8.
Cherry J, et al. Effect of gibberellic acid on growth and yield of corn, Agronomy J., Mar. 1960, p. 167-170.
Wittwer SH, et al., Gibberellin and higher plants: X Filed Observations with certain vegetable crops, Michigan Quarterly Bulletin, 1957, 40(2), p. 352-364.

* cited by examiner

METHODS TO INDUCE DROUGHT TOLERANCE IN CROPS

CROSS REFERENCE TO RELATED APPLICATIONS

This application claims the benefit of U.S. Provisional Application Ser. No. 61/759,063 filed Jan. 31, 2013. The entire teaching of this application is incorporated herein by reference.

FIELD OF THE INVENTION

The present invention is generally directed to methods for improving drought stress tolerance and yield of cereal grains comprising applying an effective amount of at least one gibberellin to the cereal grains during an early vegetative growth stage.

BACKGROUND OF THE INVENTION

Drought is a common abiotic stress that limits the productivity of all major crops. About 80% of the agricultural land in the United States experienced drought in 2012, impacting 70-75% of corn and soybean acreage (United States Department of Agriculture, Economic Research Service, 2012). According to the United Nations, drought intensity is increasing worldwide (United Nations News Center, 2012). Even seasonal mild or moderate drought in critical growth stages can reduce yields by 10-20% on rain-fed farms or those with limited irrigation. According to the National Climatic Data Center, both moderate and severe to extreme drought is becoming more common. Coupled with the increasing depletion of water resources, there is a need for new products and solutions to meet drought stress. Several approaches are being used with varying levels of success to address this problem including agronomics, traditional plant breeding, genetic engineering and chemical treatments. Each of these strategies has potential benefits, but also significant shortcomings.

There are a number of cultural practices in crop production designed to help avoid drought effects. A "drought escape" strategy can be employed by planting suitable varieties early in the season so they mature before the onset of late summer drought. A "drought avoidance" strategy can be used by selecting plant varieties with a deep root system, reduced leaf area and/or rapid stomatal closure. These strategies may have undesirable consequences. Drought escape involves a shortened or shifted growing season, while drought avoidance mechanisms may divert carbon into non-harvestable sinks Plant breeders incorporate drought tolerance traits into crops as a part of regular yield improvement programs. However, the process of breeding is slow and labor-intensive even when assisted by molecular markers. Recent breeding efforts by the seed industry have resulted in elite hybrids with 10-15% greater yield under moderate drought.

Genetic engineering offers precise tools to alter plant traits. Since the late 1990s, transgenic expression of "drought tolerance" genes has been pursued as a method of boosting crop performance under drought. For example, Monsanto Company's Genuity° DroughtGard™ Hybrid corn was approved by the United Stated Department of Agriculture and United Stated Environment Protection Agency for commercial cultivation. This hybrid corn has demonstrated a ~6% yield increase under moderate drought.

Chemicals that have been promoted and used commercially to alleviate the effects of drought include abscisic acid, anti-transpirants, and triazole growth inhibitors (e.g. uniconazole). For example, anti-transpirants reduce gas exchange and thus inhibit water loss. However, reduction of gas exchange inhibits photosynthesis, and thus slows plant growth. Although these chemicals may be effective at combating drought, they may not be acceptable for use in field crops due to negative effects on yield, cost, adverse side effects, or short duration of effect.

Accordingly, there is a need for new methods to improve cereal grain response to drought stress and to improve yield of cereal grains.

SUMMARY OF THE INVENTION

In one aspect, the present invention is directed to methods for improving drought stress tolerance of a cereal grain comprising applying an effective amount of at least one gibberellin to the cereal grain during the early vegetative growth stage.

In a further aspect, the present invention is directed to methods for improving yield of a cereal grain comprising applying an effective amount of at least one gibberellin to the cereal grain during the early vegetative growth stage.

DETAILED DESCRIPTION OF THE INVENTION

Unexpectedly, Applicants found that when a gibberellin was applied to cereal grains during the early vegetative stage, the cereal grains had greater yield and improved resistance to drought stress.

Specifically, Applicants were surprised that when they applied gibberellic acid ("GA3") to corn plants by foliar spray applications during plant development between the second and sixth leaves (V2-V6 growth stages) the plants became more resistant to subsequent drought stress. This was unexpected because one skilled in the art would predict that GA3 application would increase the susceptibility of plants to drought. The reasons why this result was unexpected are explained below.

Gibberellins are naturally-occurring plant hormones involved in most phases of plant growth and development including germination, cell proliferation, cell elongation, bud break, flowering, sex determination, fruit set, seed development and senescence (reviewed in Olszewski et al., *Gibberellin Signaling: Biosynthesis, Catabolism, and Response Pathways,* The Plant Cell, S61-S80, Supplement 2002). GA3 is well-known for its promotion of plant growth and has been used in agriculture since the early 1960's. The major commercial uses of gibberellins include thinning and sizing of seedless table grapes, enhancement of fruit size and firmness, stimulation of growth and increased yield of pasture grasses, promotion of fruit set, and advancement of flowering in horticultural crops (Sponsel, *A Companion to Plant Physiology,* Fifth Edition by Lincoln Taiz and Eduardo Zeiger, available at http://5e.plantphys.net/article.php?ch=0&id=372, 2010).

Gibberellins have not been used in efforts to improve drought tolerance because known effects of gibberellins actually teach away from the improvement of drought stress. First, GA3 application promotes leaf growth, thus increasing transpiration and water use, as was shown by Larson, et al., *RyzUp® on Cotton: Report on Trials* 1994-96, Beltwide Cotton Conference, (1997). Increased water usage increases the potential for drought stress. Second, GA3 promotion of leaf growth may occur without increased root growth (e.g., Nagel et al., *Growth rate and biomass partitioning of wildtype and low-gibberellin tomato (Solanum lycopersicum) plants growing at a high and low nitrogen supply,* Physiologia Plantarum, 111: 33-39. 2001). Increasing leaf growth without increasing root growth also increases the potential for drought stress in the plant because the plant does not have additional roots to support the vegetative growth.

In addition, because gibberellins promote plant growth and larger plants tend to use more water, there have been some attempts to reduce drought stress by negatively regulating gibberellins. In rice, corn and other cereal crops, GA3 is particularly known for its stem elongation effect which can lead to lodging. The widely popular "green revolution" genes (i.e., dwarfing genes) act by reducing gibberellin effects and thereby reducing plant growth. While the dwarfing genes of wheat prevent gibberellin signaling (Peng, et al., *'Green Revolution' Genes Encode Mutant Gibberellin Response Modulators,* Nature, volume 400, 1999), the sd1 or semi-dwarf1 genes in rice make inactive gibberellin biosynthesis enzymes (Hedden, *The Genes of the Green Revolution,* Trends in Genetics, volume 19, issue 1, 2003). Through either genetic inhibition of gibberellin biosynthesis or signaling, or anti-gibberellin chemicals, more compact plants are produced. It is thought that more compact plants should tolerate drought stress better than full sized plants.

Further, chemicals that reduce vegetative growth may minimize seedling loss during transport or after transplantation of young seedlings by reducing plant size and the demand for water. Gibberellin biosynthesis growth inhibitors act at one of four stages along the biosynthetic pathway (Rademacher, *Growth Retardants: Effects on Gibberellin Biosynthesis and Other Metabolic Pathways,* BASF Agricultural Center, 501-531, 2000). Stage 1 gibberellin biosynthesis inhibitors such as chlormequat chloride and mepiquat chloride are growth retardants that act by inhibiting synthesis of the gibberellin-precursor ent-kaurene and are used to reduce lodging of small grains and vegetative growth in cotton, respectively. The stage 1 inhibitor chlormequat chloride has long been known to induce drought resistance in corn (Robertson and Greenway, *Effects of CCC on Drought Resistance of Triticum aestivum,* and *Zea mays,* , Ann. Bot., 929-34, 1973). Stage 2 gibberellin biosynthesis inhibitors such as paclobutrazol and uniconazole inhibit gibberellin biosynthesis and are used to restrict growth of ornamental plants and vegetable seedlings. Stage 3 gibberellin biosynthesis inhibitors such as prohexadione calcium and trinexapac-ethyl are dioxygenase inhibitors that are also used to inhibit growth. Trinexapac-ethyl has been shown to induce drought tolerance in perennial ryegrass (Jiang and Fry, *Drought Responses of Perennial Ryegrass Treated with Plant Growth Regulators,* HortScience, 33 (2); 270-273, 1998). The drought tolerance imparted in corn and monocots by the gibberellin biosynthesis inhibitors and the green revolution genes teaches that inhibition of growth promotes drought tolerance. Therefore, it would be expected that increasing gibberellin levels in plants, either through changes in gene expression or exogenous application, should increase the sensitivity of corn to drought.

Accordingly, the potential ability of gibberellins, and specifically GA3, to increase cereal grains' tolerance to seasonal drought stress and grain yields has not been previously demonstrated.

Despite all of these teachings, Applicants unexpectedly found that early season application of a gibberellin primes corn seedlings to better tolerate drought occurring later in the growing season, providing a substantial yield advantage in both silage and grain corn varieties. This growth stimulation-mediated drought preparedness effect enhances effective water use under a range of drought stresses, from seasonal, mild water stress to severe, prolonged drought. This range of water stress situations is usually accompanied by heat stress.

In one embodiment, the present invention is directed to methods for improving drought stress tolerance of a cereal grain comprising applying an effective amount of at least one gibberellin to the cereal grain during early vegetative growth stage.

In a preferred embodiment, the cereal grains are corn, rice, wheat, barley, sorghum, millet, oats, triticale, rye, buckwheat, fonio, or quinoa. In a more preferred embodiment, the cereal grains are corn, rice, wheat, and sorghum. In another preferred embodiment, the cereal grain is corn. The cereal grain of the present invention may be genetically modified (GM) or non-GM.

In an embodiment, the gibberellin is gibberellin 1, GA3, gibberellin 4, gibberellin 7, and a combination thereof. In a preferred embodiment, the gibberellin is GA3 or a combination of gibberellin 4 and 7. In another preferred embodiment, the gibberellin is GA3.

In a further embodiment, the cereal grain is corn and the early vegetative growth stage is during the V2-V6 growth stage.

In an embodiment, the effective amount is from about 1 to 30 grams of gibberellin per hectare. In a preferred embodiment, the effective amount is from about 3 to 20 grams of gibberellin per hectare. In a more preferred embodiment, the effective amount is from about 6 to 16 grams of gibberellin per hectare. In a most preferred embodiment, the effective amount is from about 8 to 16 grams of gibberellin per hectare. In a preferred embodiment, GA3 is applied at from about 1 to about 30, preferably from about 3 to about 20, from about 6 to about 16, and from about 8 to about 16 grams (from about 3.2 to about 6.4 grams of GA3 per acre) per hectare.

In another embodiment, the gibberellin is applied with at least one herbicide, fungicide, insecticide, fertilizer or plant growth regulator that is not a gibberellin. In a preferred embodiment, the gibberellin is applied with at least one plant growth regulator other than a gibberellin.

In another embodiment, the herbicides include but are not limited to, glyphosate, mesotrione, halosulfuron, saflufenacil or dicamba.

In a further embodiment, the fungicides include but are not limited to tetraconazole, metconazole, a strobilurin, or a combined strobilurin-azole product.

In another embodiment, the insecticides include but are not limited to methylparathion, bifenthryn, esfenvalerate, lorsban, carbaryl or lannate.

In yet another embodiment, the foliar fertilizers include but are not limited to CoRoN (available from Helena Chemical), a controlled-release nitrogen, or BioForge (available from Stoller USA), which is largely N,N'-diformyl urea, or other micro nutrient-containing sprays.

In an embodiment, the plant growth regulators include but are not limited to, abscisic acid, aminoethoxyvinylglycine, 6-benzyladenine, jasmonic acid, napthylacetic acid or salicylic acid.

In yet another embodiment, the present invention is directed to methods for improving yield of a cereal grain comprising applying an effective amount of at least one gibberellin to the cereal grain during early vegetative growth stage.

In a preferred embodiment, the cereal grains are corn, rice, wheat, barley, sorghum, millet, oats, triticale, rye, buckwheat, fonio, or quinoa. In a more preferred embodiment, the cereal grains are corn, rice, wheat, and sorghum. In another preferred embodiment, the cereal grain is corn. The cereal grain of the present invention may be genetically modified (GM) or non-GM.

In an embodiment, the gibberellin is gibberellin 1, GA3, gibberellin 4, gibberellin 7, and a combination thereof. In a preferred embodiment, the gibberellin is GA3 or a combination of gibberellin 4 and 7. In another preferred embodiment, the gibberellin is GA3.

In a further embodiment, the cereal grain is corn and the early vegetative growth stage is during the V2-V6 growth stage.

In an embodiment, the effective amount is from about 1 to 30 grams of gibberellin per hectare. In a preferred embodiment, the effective amount is from about 3 to 20 grams of gibberellin per hectare. In a more preferred embodiment, the effective amount is from about 6 to 16 grams of gibberellin per hectare. In a most preferred embodiment, the effective amount is from about 8 to 16 grams of gibberellin per hectare. In a preferred embodiment, GA3 is applied at from about 1 to about 30, preferably from about 3 to about 20, from about 6 to about 16, and from about 8 to about 16 grams (from about 3.2 to about 6.4 grams of GA3 per acre) per hectare.

In another embodiment, the gibberellin is applied with at least one herbicide, fungicide, insecticide, fertilizer or plant growth regulator that is not a gibberellin. In a preferred embodiment, the gibberellin is applied with at least one plant growth regulator other than a gibberellin.

In another embodiment, the herbicides include but are not limited to glyphosate, mesotrione, halosulfuron, saflufenacil or dicamba.

In a further embodiment, the fungicides include but are not limited to tetraconazole, metconazole, a strobilurin, or a combined strobilurin-azole product.

In another embodiment, the insecticides include but are not limited to methylparathion, bifenthryn, esfenvalerate, lorsban, carbaryl or lannate.

In yet another embodiment, the foliar fertilizers include but are not limited to CoRoN (available from Helena Chemical), a controlled-release nitrogen, or BioForge (available from Stoller USA), which is largely N,N'-diformyl urea, or other micro nutrient-containing sprays.

In an embodiment, the plant growth regulators include but are not limited to abscisic acid, aminoethoxyvinylglycine, 6-benzyladenine, jasmonic acid, napthylacetic acid or salicylic acid.

It is suspected that the methods of the present invention work by inducing a growth burst by single or multiple applications of at least one gibberellin alone when crop growth is not limited by soil moisture. This produces a plant that is primed to better tolerate drought stress later in the growing season.

The GA3 can be applied by any convenient means. Those skilled in the art are familiar with the modes of application that include foliar applications such as spraying, dusting, and granular applications; and soil applications including spraying, in-furrow treatments, or side-dressing.

Aqueous spray solutions utilized in the present invention generally contain from about 0.01% to 0.5% (v/v) of a surface-active agent.

The surface active agent comprises at least one non-ionic surfactant. In general, the non-ionic surfactant may be any known non-ionic surfactant in the art. Suitable non-ionic surfactants are in general oligomers and polymers. Suitable polymers include alkyleneoxide random and block copolymers such as ethylene oxide-propylene oxide block copolymers (EO/PO block copolymers), including both EO-PO-EO and PO-EO-PO block copolymers; ethylene oxide-butylene oxide random and block copolymers, C2-6 alkyl adducts of ethylene oxide-propylene oxide random and block copolymers, C2-6 alkyl adducts of ethylene oxide-butylene oxide random and block copolymers, polyoxyethylene-polyoxypropylene monoalkylethers, such as methyl ether, ethyl ether, propyl ether, butyl ether or mixtures thereof; vinylacetate/vinylpyrrolidone copolymers; alkylated vinylpyrrolidone copolymers; polyvinylpyrrolidone; and polyalkyleneglycol, including the polypropylene glycols and polyethylene glycols. Other non-ionic agents are the lecithins; and silicone surface active agents (water soluble or dispersible surface active agents having a skeleton which comprises a siloxane chain e.g. Silwet L77.®.). A suitable mixture in mineral oil is ATPLUS 411 F.®.

Applicants have referred to corn developmental stages throughout the application as "V" stages. The "V" stages are designated numerically as V1, V2, V3, etc. In this identification system of V(n), (n) represents the number of leaves with visible collars. Each leaf stage is defined according to the uppermost leaf whose leaf collar is visible. "VT" refers to tassel emergence growth stage and is not an early vegetative stage of corn.

As used herein, "drought stress tolerance" refers to mitigating the effects of water shortage to the cereal.

As used herein, "silage" is a certain type of storage forage. Generally, silage is being made from plants in a process called ensilage. During this process, plants or plant parts undergo anaerobic fermentation converting sugars to acids in the crop material making the forage preservable. Depending on the plants used, other names instead of silage are employed, e.g., oatlage for oats or haylage for alfalfa. Silage is widely used for feeding milk and meat-producing animals such as dairy and beef cattle.

As used herein, "effective amount" refers o the amount of the gibberellin that will improve drought stress tolerance or improve yield. The "effective amount" will vary depending on the gibberellin concentration, the cereal(s) being treated, the severity of the drought, the result desired, and the life stage of the cereal(s), among other factors. Thus, it is not always possible to specify an exact "effective amount." However, an appropriate "effective amount" in any individual case may be determined by one of ordinary skill in the art.

As used herein, "cereal" or "cereal grain" refers to a grass that is cultivated for the edible components of its grain. Cereals are members of the monocot family Poaceae.

As used herein, "early vegetative growth stage" refers to the growth stage that begins at germination and ends when the plant is 50% of the mature plant size.

As used herein, "improving" means that the cereal grain has more of the quality than the cereal grain would have had it if it had not been treated by methods of the present invention.

The disclosed embodiments are simply exemplary embodiments of the inventive concepts disclosed herein and should not be considered as limiting, unless the claims expressly state otherwise.

As used herein, all numerical values relating to amounts, weight percentages and the like are defined as "about" or "approximately" each particular value, namely, plus or minus 10% (±10%). For example, the phrase "at least 5% by weight" is to be understood as "at least 4.5% to 5.5% by weight." Therefore, amounts within 10% of the claimed values are encompassed by the scope of the claims.

The articles "a", "an" and "the" are intended to include the plural as well as the singular, unless the context clearly indicates otherwise.

The following examples are intended to illustrate the present invention and to teach one of ordinary skill in the art how to use the formulations of the invention. They are not intended to be limiting in any way.

EXAMPLES

Example 1

A replicated corn silage study was conducted in 2012. Corn was planted on May 18, 2012, and treated with two rates of GA3 at either the V2 (June 2) or V5 (June 18) growth stage, each time at two rates of GA3. Grain yields were estimated from harvests of 20 feet of row and converted to bushels of grain per acre. There was 1.5 inches of rain in the two weeks before planting but no rain from May 10 until May 29, when there was 0.7 inch rain. During June there was 2.9 inches of rain spread over the month. There were only two rain events from July 1-25, each of less than 0.2 inches. On July $26^{th}$ there was approximately 2 inches of rain. Rainfall in June, July and August was about one third below the 30-year average for the area and the corn was under moderate drought conditions. Crop moisture conditions in July were described as 'excessively dry' by the National Climate Data Center of NOAA.

As can be seen from the silage yields in Table 1 all rates and application timings of GA3 increased the production of corn.

TABLE 1

Corn Trial

| Treatment | Application Timing | Grain Yield (Bu/Acre) |
|---|---|---|
| Untreated | N/A | 124.0 |
| 3.2 grams GA3/acre | V2 | 141.2 |
| 6.4 grams GA3/acre | V2 | 141.1 |
| 3.2 grams GA3/acre | V5 | 143.0 |
| 6.4 grams GA3/acre | V5 | 156.1 |

Example 2

In a replicated trial conducted in 2012, the corn crop experienced extreme and exceptional drought in July, as described by the National Climate Data Center. Corn was planted at the end of April and treated with GA3 at either the V2 or V5 growth stages. Thirty two days after application, the GA3-treated corn was approximately 10 inches taller than the untreated on average. Although yields at harvest were significantly lower than 'normal' due to the drought, GA3 applied at the V2 to V5 stage, several weeks before the onset of drought, had a positive impact on yield versus untreated corn (Table 2).

TABLE 2

Corn Trial

| Treatment | Application Stage | Grain Yield (Bu/Acre) |
|---|---|---|
| Untreated | N/A | 88.45 |
| 3.2 grams GA3/acre | V2 | 119.70 |

TABLE 2-continued

Corn Trial

| Treatment | Application Stage | Grain Yield (Bu/Acre) |
|---|---|---|
| 6.4 grams GA3/acre | V2 | 119.83 |
| 3.2 grams GA3/acre | V5 | 155.65 |
| 6.4 grams GA3/acre | V5 | 121.60 |

Example 3

In another field trial conducted in 2012 a time course of GA3 applications was performed. In this trial, hybrid corn was planted on April 24, 2012 at a density of 32,000 plants/acre. The plants were sprayed with GA3 at either the fifth leaf (V5) or tassel emergence (VT) on June 6 or July 7, respectively. This trial was subjected to extreme and exceptional drought in July during set and grain fill. As is shown in Table 3 below, the effect of the spray treatments of GA3 was dependent on the timing of the GA3 application. That is, GA3 application at the V5 spray timing was superior to the spray application at VT to increase grain yield. This result is unexpected and surprising, as applications of other plant growth regulators or agrochemicals with plant growth regulator effects on corn, such as the fungicide, pyraclostrobin show the greatest yield increases when applications are made around tassel emergence (VT).

TABLE 3

Corn Trial

| Treatment | Application Stage | Grain Yield (Bu/Acre) |
|---|---|---|
| Untreated | N/A | 116 |
| 5.3 grams GA3/acre | V5 | 155 |
| 5.3 grams GA3/acre | VT (tassel emergence) | 131 |

Example 4

In this trial a commercial corn hybrid was planted on Apr. 12, 2012. At six weeks after planting, the plants were at the V5-V6 developmental stage when spray treatments were applied. The experiment was conducted with three replicates and the GA3 at 6.4 grams/acre was applied in a mixture with the fungicide Domark® (available from Valent BioSciences Corporation, contains Tebuconazole) at 15 gallons/acre (at 26.8 grams/acre). Harvestable yield was estimated by the collection of harvestable ears on Jul. 30, 2012. The National Climate Data Center Palmer Index characterized the drought at spray timing (mid to late May) at mid range (less than moderate), but by the end of June (5 weeks after application) this site was under extreme drought. The corn yields were low in this trial due to lack of water, but the treatment with GA3 resulted in more bushels/acre than the untreated (see Table 4).

TABLE 4

Yield Estimate from Field Trial

| Treatment | Timing | Yield Bu/Acre |
|---|---|---|
| UTC | — | 117.1 |
| GA3 + Domark ® | V5-6 | 133.3 |

The invention claimed is:

1. A method of improving drought stress tolerance of corn comprising applying 1 to 30 grams of gibberellin 3 per hectare to corn during the V2 to V6 growth stage of the corn and when corn growth is not limited by lack of soil moisture and wherein drought stress tolerance is improved for at least 30 days after application and wherein corn yield is improved by at least 13%.

2. The method of claim 1 wherein from about 3 to 20 grams of gibberellin 3 per hectare is applied to the corn.

3. The method of claim 1 wherein from about 6 to 16 grams of gibberellin 3 per hectare is applied to the corn.

4. The method of claim 1 wherein from about 8 to 16 grams of gibberellin 3 per hectare is applied to the corn.

5. The method of claim 1 wherein the gibberellin 3 is applied with at least one herbicide, fungicide, insecticide, fertilizer or plant growth regulator that is not gibberellin3.

6. The method of claim 5 wherein the gibberellin 3 is applied with a plant growth regulator.

* * * * *